(12) United States Patent
Carboni et al.

(10) Patent No.: US 12,291,408 B2
(45) Date of Patent: May 6, 2025

(54) TRANSFER DEVICE, PARTICULARLY FOR A PACKING MACHINE

(71) Applicant: G.D S.P.A., Bologna (IT)

(72) Inventors: Salvatore Carboni, Bologna (IT); Antonio Vitali, Bologna (IT)

(73) Assignee: G.D S.P.A., Bologna (IT)

( * ) Notice: Subject to any disclaimer, the term of this patent is extended or adjusted under 35 U.S.C. 154(b) by 50 days.

(21) Appl. No.: 17/998,022

(22) PCT Filed: Jul. 5, 2021

(86) PCT No.: PCT/IB2021/055999
§ 371 (c)(1),
(2) Date: Nov. 4, 2022

(87) PCT Pub. No.: WO2022/009064
PCT Pub. Date: Jan. 13, 2022

(65) Prior Publication Data
US 2023/0331497 A1    Oct. 19, 2023

(30) Foreign Application Priority Data
Jul. 9, 2020  (IT) .................... 102020000016630

(51) Int. Cl.
*B65G 47/91*   (2006.01)
*B65B 35/38*   (2006.01)

(52) U.S. Cl.
CPC ............ *B65G 47/918* (2013.01); *B65B 35/38* (2013.01)

(58) Field of Classification Search
None
See application file for complete search history.

(56) References Cited

U.S. PATENT DOCUMENTS

| | | | |
|---|---|---|---|
| 4,977,727 A | 12/1990 | Milleson | |
| 6,467,608 B2 * | 10/2002 | Stauber | B65G 19/025 198/460.2 |
| 9,908,646 B2 * | 3/2018 | Renner | B65B 35/36 |
| 11,713,147 B2 * | 8/2023 | Duperray | B65G 47/53 198/469.1 |
| 11,964,830 B2 * | 4/2024 | McCoy, Jr. | B65G 47/917 |
| 2012/0233967 A1 | 9/2012 | Bellante | |
| 2017/0036794 A1 | 2/2017 | Sassi et al. | |
| 2019/0255698 A1 * | 8/2019 | Zeiner | B25J 5/02 |
| 2022/0142190 A1 * | 5/2022 | Rusko | A22C 25/16 |

OTHER PUBLICATIONS

International Search Report and Written Opinion for International Application No. PCT/IB2021/055999 filed on Jul. 5, 2021 on behalf of G.D S.P.A. Mail Date: Oct. 20, 2021 12 pages.

* cited by examiner

*Primary Examiner* — Kavel Singh
(74) *Attorney, Agent, or Firm* — Steinfl + Bruno LLP (57) ABSTRACT

A transfer device to transfer articles by removing the articles from a removal zone and depositing the articles in a discharge zone, wherein a support plane and a deposit direction substantially perpendicular to the support plane are defined at the discharge zone. The transfer device includes a gripping head with retention elements, each for retaining a respective article, and a movement mechanism configured to move at least one retention element with respect to at least one other retention element in a staggering direction having a non-null component parallel with the deposit direction.

15 Claims, 5 Drawing Sheets

TRANSFER DEVICE, PARTICULARLY FOR A PACKING MACHINE

CROSS REFERENCE TO RELATED APPLICATIONS

The present application is the US National Stage of International Patent Application No. PCT/IB2021/055999, filed on Jul. 5, 2021, which in turn, claims priority to Italian Application No. IT 102020000016630, filed on Jul. 9, 2020.

The present invention relates to a transfer device, particularly configured for use thereof in a packing machine for articles.

It is also directed to a packing machine comprising such a transfer device and a method for packing articles.

The present invention finds a preferred, though not exclusive, application in the field of canned packing of loose articles, such as capsules for products by infusion, for example coffee, a field to which reference may be made hereafter without loss of generality.

In particular, in the relevant technical sector, packing machines are known which comprise a transfer device suitably configured to transfer the articles to be packed by removing them from a removal zone and depositing them in a discharge zone, which may be located at a container to be filled.

In a known embodiment, such transfer devices may comprise a gripping head, which mounted on a movable arm and is provided with one or more retention elements capable of retaining in engagement the articles to be transferred from the removal zone to the discharge zone.

Transfer devices are also known which, before depositing the removed articles, are able to bring them close to one another so as to promote the insertion thereof into the container to be filled.

In this description as well as in the accompanying claims, certain terms and expressions are deemed to have, unless otherwise expressly indicated, the meaning expressed in the following definitions.

The term "article" means any solid product which, within an industrial production line, can be removed, moved and deposited by a transfer device.

In particular, the transfer device may be configured to remove such product (or a plurality of such products) from a supply line and deposit it in a container which is provided for the transfer thereof or packing thereof.

The articles can be identical to each other, or they can differ from each other in some characteristics such as the formation, the composition, the colour or their orientation.

The articles can be, for example, food and confectionery products already packed in individual containers or wrappers, such as coffee capsules or other infusion drinks, bottles and cartons of beverages, yoghurt pots, individual so chocolates (wrapped or bare), candies, small boxes, pouches containing solid, liquid or semi-solid food products; moreover, products of the ceramic industry, absorbent products for hygienic use, products of the tobacco industry, products of the cosmetic industry, products of the pharmaceutical industry, products of the personal & home care industry.

The term "loose" referring to articles means a plurality of single articles which are separated and not secured to each other, so that each of them can be moved and treated independently of the other articles.

A plurality of articles is moved, removed, deposited or otherwise treated "in group" when all the articles of the plurality are moved, removed, deposited, or otherwise treated, in the same time interval or, in other words, simultaneously.

For example, the articles are rotated "in groups" when they all begin and end a rotation movement at substantially the same instant.

The term "container" means any receptacle that is suitable for containing articles, in particular any receptacle in which the transfer device deposits the articles removed. Preferably the container is a receptacle which is suitable for packing a group of articles. Even more preferably the container is for example a box, a tray or a pallet or a drawer, which is however intended to contain a group of articles in an advantageously sorted manner.

A first direction is said "substantially" perpendicular to a second direction when they are inclined to each other through an angle between 80° and 100°. Similarly, two directions are said "substantially" parallel when they are inclined to each other as far as a maximum of 10°.

The term "component" of a first direction with respect to a second direction so means the orthogonal projection of the first direction onto the second direction, when both directions are made coplanar.

In particular, a first direction has a component which is parallel to a second "non-null" direction when the orthogonal projection of the first direction onto the second direction is different from zero or, in other words, when the first direction is not perpendicular to the second direction.

It is also specified that the expression "moving an object between a first position and a second position" means both the movement from the first position to the second position and the movement from the second position to the first position.

This definition applies equally to similar expressions of movement, such as for example transferring or moving a generic object between two positions or between two zones or even between two different operating configurations.

When a plurality of objects are in a coplanar configuration, any direction incident to the plane defined by that plurality of objects is defined as the "staggering direction". To define a coplanar configuration, the plurality of objects comprises at least three objects. The Applicant has observed that, in some known transfer devices, the retention elements may be brought close to one another so as to compact the articles into a grouped arrangement before being deposited in the discharge zone.

In this way, the articles can be deposited in containers as small as possible, minimising space requirements and, consequently, production, storage and distribution costs.

In addition, when the articles are moved into the grouped arrangement they can be more easily inside a box-shaped container, intended for their so packaging.

In the latter case, in particular, the Applicant has verified that the most delicate step of inserting the articles into a box is the initial moment of the insertion, when the articles may abut the upper edge of the box walls, with the risk of jamming and damaging the box.

The Applicant has observed, however, that the movement of the retention elements brought close to one another takes place within a plane substantially parallel to the support plane on which the articles are intended to be deposited.

The Applicant has therefore perceived that the degree of compactness of the articles in a grouped arrangement can be further increased by allowing the retention elements to move also in directions other than those that are parallel to the support plane of the discharge zone.

Finally, the Applicant has found that by arranging a transfer device so that the retention elements can be moved on the gripping head in a differentiated manner along a direction substantially perpendicular to the support plane, even more compact grouped arrangements of the articles can be obtained and thus effectively respond to the constant need to minimise the size of the packing containers, and further promote the step of insertion of the articles inside a container.

In a first aspect thereof, therefore, the present invention is directed to a transfer device which is provided to transfer a plurality of articles by removing them from a removal zone and depositing them in a discharge zone.

Preferably, a support plane is defined at said discharge zone.

Preferably, a deposit direction substantially perpendicular to said support so plane is defined at said discharge zone.

Preferably, said transfer device comprises a gripping head which is movable between said removal zone and said discharge zone.

Preferably, said gripping head is provided with a plurality of retention elements.

Preferably, each retention element is provided in order to retain a respective article of said plurality of articles.

Preferably, said transfer device comprises a movement mechanism which is provided to move at least one of said retention elements with respect to at least one other of said retention elements in a staggering direction.

Preferably, said staggering direction has a non-null component which is parallel with said deposit direction.

Thanks to these features, the transfer device according to the present invention is able to obtain even more compact configurations of articles when deposited in the discharge zone.

In particular, thanks to the present invention, some particular conformations of the articles can be advantageously exploited, for example when they present tapered conformations or, more generally, conformations with variable section in the deposit direction. In fact, by staggering the articles between them in this direction, it is possible to identify mutual positions that allow a greater degree of approach between the articles.

In particular, this advantage is clearly appreciable when the articles have a truncated cone or truncated pyramidal shape, for example, and even more so when they are arranged one next to the other in an alternating upright and upturned position.

Moreover, the feature object of the present invention may be advantageous also in case of articles with constant cross-section, for example by moving one or more articles with respect to the others through a measure which is greater than their own size in the deposit direction so as to create space for the approach of the other articles, possibly by repositioning the moved articles in a coplanar relationship once all the articles are even partially inserted in the box.

In a second aspect thereof, the present invention relates to a packing machine for articles, comprising at least one transfer device which is provided to remove a plurality of said articles from a removal zone and deposit them in a discharge zone, and realised according to the first aspect.

The packing machine according to the present invention can therefore advantageously pack articles in smaller containers and/or deposit them in the container with a greater safety margin, thus enabling a reduction in waste during packing and an increase in production capacity.

In a third aspect thereof, the present invention relates to a method for transferring a plurality of articles from a removal zone to a discharge zone.

Preferably, a support plane is defined at said discharge zone.

Preferably, a deposit direction substantially perpendicular to said support plane is defined at said discharge zone.

Preferably, the method envisages the step of providing a transfer device comprising a gripping head provided with a plurality of retention elements.

Preferably, the method envisages the step of removing said plurality of articles from said removal zone by means of said plurality of retention elements.

Preferably, the method envisages the step of moving at least one of said retention elements with respect to at least one other of said retention elements in a staggering direction having a non-null component which is parallel with said deposit direction.

Preferably, the method envisages the step of moving said retention elements inside a reference plane which is substantially perpendicular to said deposit direction between a first configuration, in which said retention elements are spaced apart from one another, and a second configuration, in which said retention elements are brought close to one another.

Preferably, the method envisages the step of depositing said articles on said support plane.

In a fourth aspect thereof, the present invention relates to a method for packing a plurality of articles in a container, wherein said articles are transferred into said container in accordance with the transfer method of the third aspect.

In a fifth aspect thereof, the present invention relates to a transfer device for articles which is provided to transfer a plurality of articles by removing them from a removal zone and depositing them in a container, and comprising a gripping head which is movable between said removal zone and said container.

Preferably, said gripping head is provided with a plurality of retention elements which are provided to retain an article of said plurality.

Preferably, said transfer device comprises at least one spreader element which extends from said movable gripping head in accordance with said retention elements and is provided to abut said container.

Preferably, said spreader element is provided to abut said container said so container at one of the walls thereof or at one of the closing panels thereof.

In this way, the opening of the container can be widened and it is easier to insert articles inside it.

In particular, the Applicant has observed that by suitably abutting even just the closing panel, it is possible to temporarily deform the opening of the container by widening it.

In fact, the Applicant has noted that, following the pressure exerted by the spreader element on the closing panel, the latter tends to bend, thereby also bending the creasing line which connects it to a wall of the container and which defines the axis about which it normally rotates with respect to that wall in order to close or open the container.

However, when the creasing line is bent, it is no longer suitable for defining a rotation axis and, de facto, the rotation of the closing panel with respect to the wall is prevented. Not only that, in this condition, the closing panel and the wall connected thereto become almost integral, so much so that the curvature of the closing panel is transmitted to the wall to which it is connected, causing the opening of the container to widen.

Appropriately, the deformation carried out by the spreader element is done so as to be completely reversible, in such a manner that when the spreader element is removed from the closing panel, the latter returns to its initial configuration and can rotate normally about the creasing line.

This feature is particularly advantageous as it allows the spreader element to be kept further spaced apart from the gripping elements and, above all, at a higher elevation with respect to the support plane of the articles, so as to avoid any possible interference with the removal and deposit operations so carried out by the gripping head.

In a sixth aspect thereof, the present invention relates to a method for depositing a plurality of articles in a container comprising:
  providing a transfer device comprising a gripping head for transferring a plurality of articles by removing them from a removal zone and depositing them in said container and which is movable between said removal zone and said container
  removing a plurality of articles from a removal zone
  moving said gripping head towards said container
  temporarily widening an opening of said container by means of at least one spreader element,
  depositing said plurality of articles inside said container through said widened opening.

Preferably, said opening is widened by abutting said container at one of the closing panels thereof.

Preferably, said opening is widened by bending a creasing line which is provided between a closing panel of said container and a wall of said container connected to said closing panel.

The present invention, in at least one of the aforesaid aspects, may have at least one of the further preferred features set out below.

Preferably, the articles are loose, so they are removed from the removal zone, transferred and deposited in the discharge zone by the retention elements of the gripping head independently of each other.

Preferably, the articles are transferred in groups from the removal zone to the discharge zone, and, again in groups, are deposited in the discharge zone.

In one embodiment, the articles are further removed in group.

In another embodiment, the articles can be removed from the removal zone in successive steps.

In other words, the articles can be removed from the removal zone either simultaneously in a single group, or in subgroups during successive steps and forming the final group only at the end of these steps.

In this way, the articles can be arranged on the gripping head in configurations that are different from those in the removal zone, which greatly allows to increase the operating flexibility of the packing machine.

Preferably, said retention elements comprise first retention elements and second retention elements and said movement mechanism is provided to simultaneously move said first retention elements with respect to said second retention elements in said staggering direction.

In this way, two groups of retention elements are formed, minimising the components to jointly move the retention elements of one group with respect to the retention elements of the other group. In addition, this feature allows the movements and trajectories of the various retention elements to be managed uniformly, without placing an excessive burden on the movement mechanism of the gripping head.

Preferably, said first retention elements during the movement in said staggering direction are coplanar with each other to a reference plane which is substantially perpendicular to said deposit direction.

In this way, the first retention elements are moved while maintaining a condition of parallelism to the support plane on which they are intended to rest, simplifying the management of their movements.

Preferably, said first retention elements are moved in said staggering direction between a first position, in which said first retention elements are coplanar with said second retention elements, and a second position, in which said first retention elements and said second retention elements are located in respective reference planes which are parallel with and spaced apart from one another.

In this way, by moving the first retention elements to the first position, it is possible to effectively remove the articles from the removal zone where they are generally coplanar with each other, and then after moving the first retention elements to the second position, it is possible to proceed to bring the articles close to one another in a grouped arrangement with the greatest possible degree of compaction.

Naturally, the degree of movement of the first retention elements in the staggering direction is determined by the formation of the articles and will be chosen appropriately in order to allow the optimal degree of approach among the articles.

Preferably, said second retention elements are not movable in said staggering direction with respect to said gripping head.

In this way, the relative movement action between the first and second retention elements is delegated only to the first retention elements. This advantageously allows to save the components needed for the movement of the second retention elements, with consequent benefits in terms of both production costs and the lightness of the gripping head.

However, in a different embodiment, both the first and second retention elements could be provided with their similar mechanism which allows their independent movement in the staggering direction.

In a preferred embodiment, said movement mechanism comprises an actuating member for moving said first retention elements in said staggering direction.

Preferably, this actuating member is of the double-acting type.

Preferably, wherein said actuating member is of the pneumatic type.

Preferably, each of said retention elements is fixed to one end of a support rod.

Preferably, said support rod is substantially parallel to said deposit direction.

Preferably, said actuating member is provided to move said support rod of said first retention elements in said staggering direction.

Preferably, said actuating member comprises a cylinder and a piston which is slidingly engaged in said cylinder, one of which is connected to said support rod.

Thanks to these features, the movement of the retention elements in the deposit direction is achieved by a simple yet precise and reliable mechanism.

Preferably, said staggering direction is straight.

In other embodiments, the staggering direction in which the retention elements are moved may be curvilinear, for example it may be formed by an arc of circumference.

Preferably, said staggering direction is substantially parallel to said deposit direction.

In other embodiments, the staggering direction may be inclined with respect to the deposit direction, as long as it is also inclined with respect to the support plane.

Preferably, said staggering direction and said deposit direction are substantially parallel to a vertical direction.

In a preferred embodiment, said movement mechanism is further provided to move at least one of said retention elements in directions which are located in a reference plane which is substantially perpendicular to said deposit direction.

Preferably, said retention elements are moved inside said reference plane between a first configuration, in which said retention elements are spaced apart from one another, and a second configuration in which said retention elements are brought close to one another to move said plurality of articles in a grouped arrangement.

In a preferred embodiment, said gripping head removes said articles from said removal zone when said retention elements are in said first configuration and deposits said articles in said discharge zone when said retention elements are in said second configuration.

In this way, the articles can be removed when they are relatively spaced apart from one another and deposited in a grouped arrangement, which is more compact and advantageous for packing articles in a box.

In another embodiment, said gripping head removes said articles from said removal zone when said retention elements are in said second configuration and deposits said articles in said discharge zone when said retention elements are in said first configuration.

In this case, the articles are removed in a grouped arrangement and then spaced apart from one another before being deposited.

Preferably, in said plurality of retention elements, there is defined a first group of retention elements which is formed by retention elements which are moved between said first configuration and said second configuration, and a second group of retention elements which is formed by retention elements so which are not moved between said first configuration and said second configuration.

Preferably, all the retention elements of said first group of retention elements are moved between said first configuration and said second configuration by means of rotation about respective rotation axes.

In this way, the movement of the retention elements takes place thanks to a simplified movement mechanism, which makes it possible to reduce the number of components required, lightening the gripping head and consequently increasing its movement speed and the overall production capacity of the transfer device.

In a different embodiment, said retention elements are moved between the first and second configuration by means of linear actuators.

Preferably, the retention elements of said second group of retention elements are fixed with respect to said gripping head.

This makes it possible to advantageously save the movement components for this retention element, with further lightening of the gripping head.

In one embodiment, said second group of retention elements may be formed by one or more retention elements.

In this case, when the retention elements of the first group are moved into said second configuration, they are brought close to the elements of said second group.

In this way, the retention elements can be arranged and configured on the gripping head in many different ways in order to meet different packing needs. In particular, it is possible to deposit the articles in the containers according to an arrangement in separate groups.

In another embodiment, said second group of retention elements does not so comprise any retention elements.

In this case, all the retention elements are moved between said first and said second configuration.

In one embodiment, said rotation axes are substantially parallel to each other.

Preferably, said rotation axes are substantially parallel to said deposit direction.

In one embodiment, said rotation axes are aligned in successive rows.

Preferably, in each row, said rotation axes are equidistant.

Preferably, said rows of rotation axes are equidistant between them.

In this way, the rotation axes have an ordered matrix arrangement and the movement mechanism of the retention elements can be realised more easily.

In one embodiment, said retention elements, during the rotation towards said second configuration, are all moved towards a central grouping axis.

This provision makes it possible to obtain a particularly compact grouped arrangement of the articles.

In a preferred embodiment, said central grouping axis coincides with the axis of one of said retention elements.

In this case, it is envisaged that this retention element whose axis coincides with the central grouping axis does not vary its position between the first and second configuration, remaining fixed. In this case, this retention element forms the aforesaid second group of retention elements.

Preferably, the spacing of each retention element from said respective rotation axis is a function of the spacing of said rotation axis from said central grouping axis.

Preferably, during the rotation between said first configuration and said so second configuration, said retention element is rotated through approximately 1800.

In this way, the retention element is moved as far as the maximum spacing possible with a rotation movement having a predetermined radius.

Preferably, said movement mechanism comprises, for each of said retention elements which is rotated, an arm which extends perpendicularly to said rotation axis.

Preferably, said arm defines the spacing of said retention element from said rotation axis.

Preferably, in said first configuration and in said second configuration, said arm extends in a direction passing through said central grouping axis.

Preferably, said movement mechanism comprises, for each of said retention elements which is rotated, a pinion which is mounted coaxially with said respective rotation axis.

Preferably, said pinion is fixed coaxially on a shaft which is rotatably mounted on a frame of said gripping head.

More preferably, said shaft is connected to said retention element by means of said arm.

Even more preferably, said arm extends between said shaft and said support rod to which said retention element is mounted.

In a preferred embodiment, said movement mechanism comprises a plurality of racks engaged by meshing with said pinions to control the rotation of said pinions about said respective rotation axes.

Preferably, said pinions are aligned in successive rows and the pinions of each row are engaged by a respective rack.

In other words, a single rack is meshed with all the pinions in a single row, so that the number of racks that is required to move all the pinions is equal to the number of successive rows of pinions.

Preferably, said movement mechanism comprises a motor member which is connected to said plurality of racks by means of a transmission shaft.

Preferably, said transmission shaft is unique.

Thanks to each of these features, an effective, precise and, at the same time, particularly simple movement mechanism with a reduced number of components is achieved, making it even lighter.

In a preferred embodiment, said discharge zone, in which said plurality of articles are deposited, is defined in a container.

Preferably, the container is a box, comprising a bottom and lateral walls rising from the bottom towards an opening of the box.

Preferably, the bottom of the container defines said support plane of the discharge zone.

Said support plane may also be formed by a layer of articles that has been previously deposited in the container.

In one embodiment, said transfer device comprises at least one spreader element which extends from said movable gripping head in accordance with said retention elements and is provided to abut said container and to widen the opening thereof.

In this way, it is possible to widen the opening of the container facilitating the insertion of the articles inside it.

In a first embodiment, said spreader element is provided to abut said container at one of the closing panels thereof.

In this way, it is possible to keep the spreader element at a higher elevation than the support plane of the articles so as not to interfere with the operations of the gripping head, in particular by avoiding touching the plane of the first conveyor belt when the articles are only removed on some of the rows thereof.

Preferably, moreover, said spreader element is positioned centrally between two retention elements, so as not to risk interfering with the articles during the operations of the gripping head.

In a second embodiment, said at least one spreader element is provided to abut said container at one of the walls thereof.

In another embodiment, a pair of spreader elements is envisaged which are provided to abut a pair of opposite walls of said container.

In some embodiments, said at least one spreader element is movable with respect to the gripping head, between an operating position in which it is provided to abut said container and a non-operating position in which it is moved away from said gripping elements.

In a further embodiment, said at least one spreader element may be operatively associated with the conveyor that transports the container by acting on a wall or a panel for closing the container.

In one embodiment, said articles have a variable cross-section in said deposit direction.

In this way, it is always possible to identify a correct staggering between the retention elements in the deposit direction, which allows the degree of compaction to be increased when the articles are brought close to one another by moving in the plane perpendicular to the deposit direction.

Preferably, said articles have a tapered formation from a larger base as far as a smaller base.

Preferably, said articles have a substantially truncated cone formation.

Preferably, said articles have a bottom with a smaller cross-section and a head with a larger cross-section.

In a preferred embodiment, said articles are capsules of a product by infusion, e.g. coffee.

Preferably, said first retention elements have a first surface and said second retention elements have a second surface, which is smaller than said first surface.

Preferably, said first retention elements are configured to retain said articles at said head and said second retention elements are configured to retain said articles at said bottom.

Preferably, each of said first retention elements is alternated with one of said second retention elements and each of said second retention elements is alternated with one of said first retention elements.

Preferably, said first retention elements are arranged in a quincunx pattern and said second retention elements are arranged in a quincunx pattern in a manner complementary to said first retention elements.

This allows the articles to be removed with an alternating head-bottom and bottom-head orientation, enabling an effective compaction of the articles when they are moved in the grouped arrangement.

In a preferred embodiment, in said second position, the orthogonal projection of the articles which are retained by said first retention elements in a plane parallel to said deposit direction is partially superimposed on the orthogonal projection of the articles which are retained by said second retention elements only near said smaller base.

Preferably, in said second position, the orthogonal projections in a plane parallel to said deposit direction of the articles retained by the first and second retention elements respectively are superimposed through a measure between 0 and 10 mm, more preferably, between 0 and 5 mm.

In this way, the passage from the first to the second position involves moving the articles between a substantially coplanar configuration to a staggered one in which a minimum degree of interference between the articles is maintained. Consequently, when the articles are brought close to one another in the plane perpendicular to the deposit direction, they may touch each other in a narrow region close to the smaller base, avoiding superposition of adjacent articles that could prevent any subsequent repositioning of the articles in a coplanar configuration.

In a preferred embodiment, said transfer device comprises a delta-type robot including a plurality of articulated arms to the end of which said gripping head is fixed.

Preferably, said gripping head is moved by said articulated arms in trajectories that are defined by three linear movement axes.

In a preferred embodiment of embodiment, each of said retention elements can be selectively activated and deactivated in order to retain or not to retain in engagement one of said articles independently of the other retention elements.

In this way, it is possible to compose different configurations of articles on the gripping head, such as for example configurations in which there is provided a number of rows greater than that of the rows with which the articles are supplied to the transfer device, or to compose incomplete or partial configurations.

Preferably, said retention elements are connected to a pressure reduction so circuit.

Preferably, each retention element is connected to said pressure reduction circuit by means of a respective conduit and can be selectively put in communication with the pressure reduction circuit by the opening of a respective shut-off valve.

In this way, the articles are retained by the retention elements through suction.

Preferably, said conduit is formed inside said support rod.

In this way, further conduits are spared, while lightening at the same time the support rods and thus, overall, the gripping head.

In a preferred embodiment, said removal zone is defined on a first conveyor belt on which said articles are placed.

In other embodiments, the removal zone can be defined on a deposit shelf or on a temporary accumulation element (buffer) or on a container.

Preferably, said retention elements are moved into said first configuration to remove said articles from said removal zone.

In this way, the articles can be arranged on the first conveyor belt so that they are relatively spaced apart from one another, thus facilitating their movement and removal by the transfer device.

Preferably, said support plane is defined in a container.

Preferably, said container is positioned on a second conveyor belt.

In other embodiments, said support plane can be defined on a deposit shelf or a temporary accumulation element (buffer) or on a conveyor belt.

Preferably, said at least one transfer device is positioned between said first conveyor belt and said second conveyor belt.

Preferably, said at least one transfer device is operative in an area which so comprises a portion of said first conveyor belt and portion of said second conveyor belt.

This arrangement of conveyor belts and of the transfer device allows obtaining a packing machine with a particularly compact layout.

Preferably, at least in said zone in which said transfer device is operative, said first conveyor belt and said second conveyor belt are moved in respective advance directions which are substantially parallel to each other.

Preferably, said advance directions of said first conveyor belt and said second conveyor belt have opposite directions.

In a preferred embodiment, a plurality of said transfer devices are provided between said first conveyor belt and said second conveyor belt.

Preferably, said transfer devices are all aligned parallel to said advance directions.

This results in a compact machine layout, optimising the operation of the transfer devices.

In a preferred embodiment, said plurality of articles are removed by said retention elements while said removal zone is moving.

In a preferred embodiment, said plurality of articles are deposited by said retention elements on said support plane while said support plane is moving. This makes it possible to create a packing machine that operates substantially continuously, creating the optimal conditions for both reducing the number of transfer devices that are required or the need for intermediate buffers, and for increasing its production capacity.

In a preferred embodiment, said articles are brought close to said support plane of said container when said first retention elements are moved into said second position.

In this way, the articles retained by the second retention elements can be deposited on the support plane, while the articles retained by the first retention elements remain in a raised position with respect to the support plane.

In a first embodiment, the articles are then released from the retention elements.

In this way, the articles previously retained by the first retention elements can descend by gravity among the articles previously retained by the second retention elements, resting on the support plane and assuming the most suitable position inside the container, retained laterally by the lateral walls of the container.

In one embodiment, said first retention elements are subsequently moved into said first position to facilitate the deposit of the respective articles on said support plane.

In this way, the articles previously retained by the first retention elements are pushed among the articles previously retained by the second retention elements.

Preferably, said first retention articles are moved to said first position after said respective articles have been released.

Thanks to the above-mentioned characteristics, the articles transported by the first retention elements are suitably brought back into coplanarity with the articles transported by the second retention elements, and allows to obtain an appropriate arrangement of the articles inside the container and to form, possibly, an effective support plane for a subsequent layer of articles intended to be packed in the same container.

It is also provided that this operation can take place just before depositing the articles on the support plane.

The characteristics and advantages of the invention will become clearer from the detailed description of an embodiment illustrated, by way of non-limiting example, with reference to the appended drawings wherein.

With reference to the enclosed figures, 100 indicates as a whole a packing machine comprising some transfer devices 200 which are realised in accordance with the present invention.

The packing machine 100 is provided to package a plurality of articles 1, loose, within containers, which in this embodiment example consist of boxes 30, so as to prepare a finished packaging, ready for final packaging and subsequent shipment.

The articles 1 are, in this preferred embodiment example, capsules for the production of drinks by infusion, in particular coffee.

Each article 1 is formed by a substantially rigid casing, shaped like a cup, having a truncated cone form in which a bottom 2, at the smaller base thereof, and a lateral wall 3 which extends with a slight flaring towards a head 4, opposed to the bottom 2, at the larger base thereof, are defined, wherein the casing has a mouth closed by a lid such as, for example, an aluminium foil which is removably fixed to the edges of the mouth.

Figure 1:
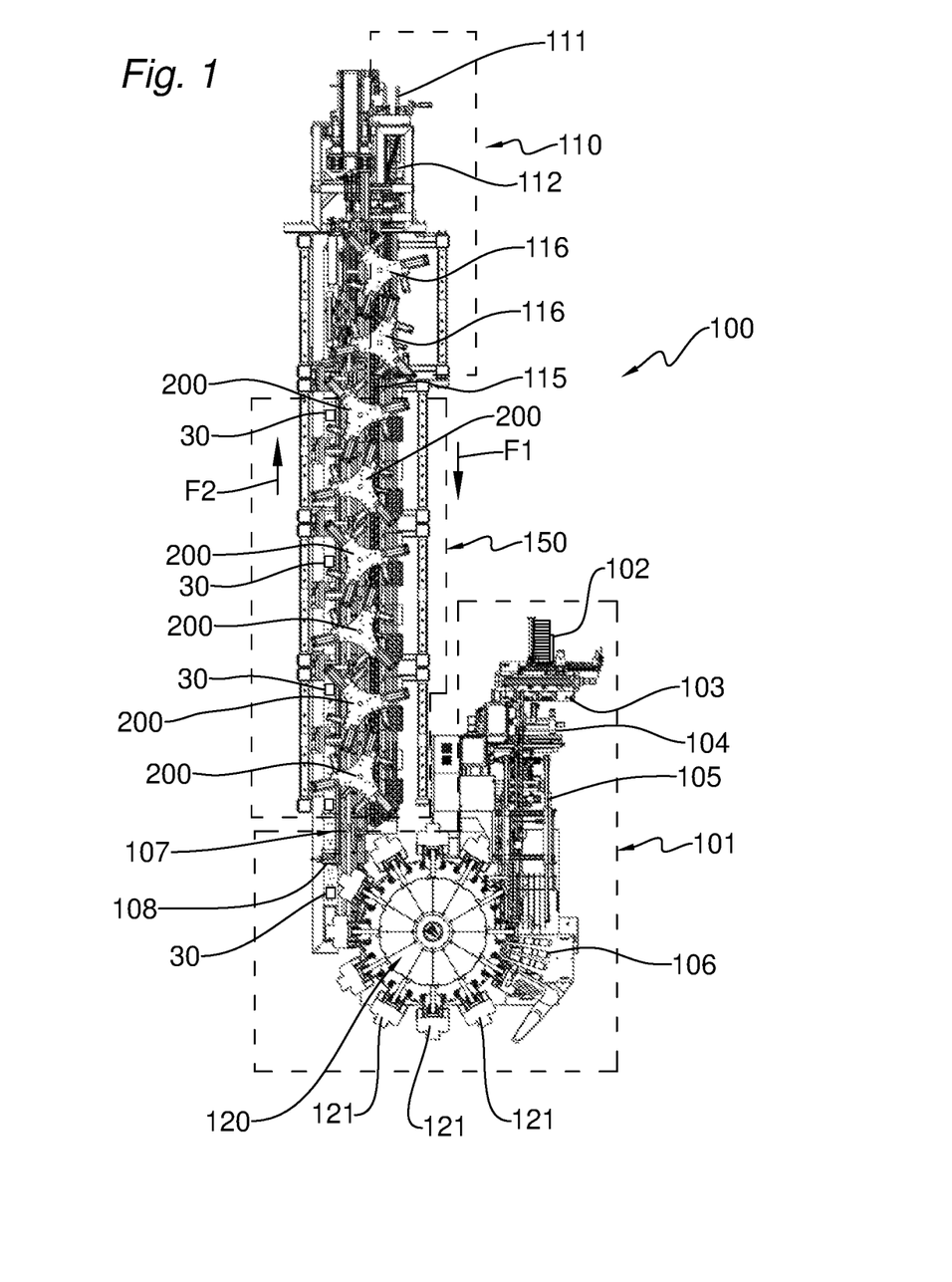
FIG. 1 is a schematic plan view from above of a packing machine for loose articles, provided with transfer devices made in accordance with the present invention.

The packing machine 100 comprises, in its most general units, a forming line 101 of the boxes 30, a sorting line 110 of the articles 1, and a packing line 150, in which the articles 1 coming from the sorting line 110 are deposited in the boxes 30 coming from the forming line 101.

The sorting line 110 is supplied with articles 1 by a first conveyor 111, which transports two rows of articles 1 in an upright position, i.e. resting on the bottom 2 and with the head 4 facing upwards.

The first conveyor 111 is connected to a first sorting station 112, comprising, for example, a pair of screw conveyors 112a, in which the articles 1 of the two so rows of articles are correctly spaced apart from one another and the articles of one of the two rows is tipped in upturned position, i.e. resting on the head 4 and with the bottom 2 facing upwards.

The articles 1 exiting the first sorting station 112 are then supplied to an intermediate conveyor 113, on which two parallel and flanked rows of articles 1 are deposited: one with the articles 1 in upright position and one with the articles 1 in upturned position.

The sorting line 110 of the articles 1 further comprises a second sorting station 114 which takes care of removing the articles 1 from the intermediate conveyor 113 and of depositing them on a first conveyor belt 115 with a predefined removal arrangement (pattern).

In the present example, also on the first conveyor belt 115 the articles 1 are arranged in two rows, and the predefined removal pattern is of the chequered type, in which each article 1 in upright position is flanked on three sides by articles 1 in upturned position, and vice versa, maintaining a constant spacing among articles 1 in the same row.

To form such a removal pattern, the second sorting station 114 comprises a pair of sorting robots 116 which are arranged in line between the first conveyor 113 and the first conveyor belt 115.

Each sorting robot 116 comprises a gripping hand which is provided to remove, by means of respective retention elements, a plurality of articles 1 which are present on a single row of the intermediate conveyor 113, which will therefore all be in upright position or all in upturned position, and transfer them onto the first conveyor belt 115.

During the transfer towards the first conveyor belt 115, the retention so elements, which are initially aligned to remove the articles 1 from a single row of the intermediate conveyor 113, are alternately staggered with each other so as to deposit the articles 1 on the one and the other row of the first conveyor belt 115 in successively alternating positions.

The two sorting robots 116 thus make up the two rows of articles 1 on the first conveyor belt 115, wherein in each row the articles 1 are alternately in upright position and in upturned position, and wherein each article in upright position in one row is flanked by an article in upturned position in the other row, thus altogether forming the desired chequered pattern.

The boxes 30 in which the articles 1 are deposited are formed in the forming line 101 from corresponding blanks 31, each of which consists of a flat semi-finished product made of foldable and semi-rigid material, for example cardboard, which is suitably cut and provided with folding creased portions.

The forming line 101 comprises a supply station 103, wherein the single blanks 31 are extracted from a stack of blanks that is supplied at an inlet 102, as well as a folding station 104, located downstream of the supply station 103, in which the blanks 31 undergo a preliminary folding of some of the flaps thereof before being transferred onto a blanks conveyor 105.

The blanks conveyor 105 crosses a gluing station 106, wherein a plurality of hot glue dispensing guns or nozzles lay suitable glue spots on the blanks 31. The forming line 101 further comprises a forming carousel 120 supplied by the blanks conveyor 105 which is provided with a plurality of forming devices 121. In the travel period of a portion of the curved tract of the forming carousel 120, the blanks 31 are suitably folded within the forming devices 121 so that the portions provided with glue spots are made to adhere to each other and to form respective boxes 30 having a respective upper closing panel so in an open position.

At the end of the curved tract of the forming carousel 120, the boxes 30 are supplied, with the opening facing upwards, onto a second conveyor belt 107. In an initial tract of the second conveyor belt 107, a station 108 is provided that takes care of folding the closing panel of the boxes 30 into an open position, in order to promote the correct filling of the boxes 30 with the articles 1. In other words, the opening position of the closing panel must be such that it does not obstruct the subsequent filling of boxes 30 with articles 1.

As mentioned above, in the packing line 150 the articles 1 coming from the sorting line 102, in particular from the first conveyor belt 115 are deposited in the boxes 30 coming from the forming line 101, in particular from the second conveyor belt 107.

Advantageously, at the packing line 150, the first conveyor belt 115 and the second conveyor belt 107 are flanked and are moved linearly in substantially parallel but opposite advance directions, indicated in FIG. 1 with F1 and F2 respectively.

Between the first conveyor belt 115 and the second conveyor belt 107 there is interposed a plurality of transfer devices 200, all of which are aligned parallel to the aforesaid advance directions.

The number of transfer devices 200 is a function of the number of articles intended to be deposited in the single boxes and the speed of conveyor belts 107 and 115.

Each transfer device 200 is provided to remove a plurality of articles 1 from a respective removal zone and deposit it in a respective discharge zone.

In particular, each transfer device 200 removes a plurality of articles 1 from so the first conveyor belt 115 when it crosses the respective removal zone and deposits them in a box 30 which is transported on the second conveyor belt 107 as it crosses the respective discharge zone.

Figure 2:
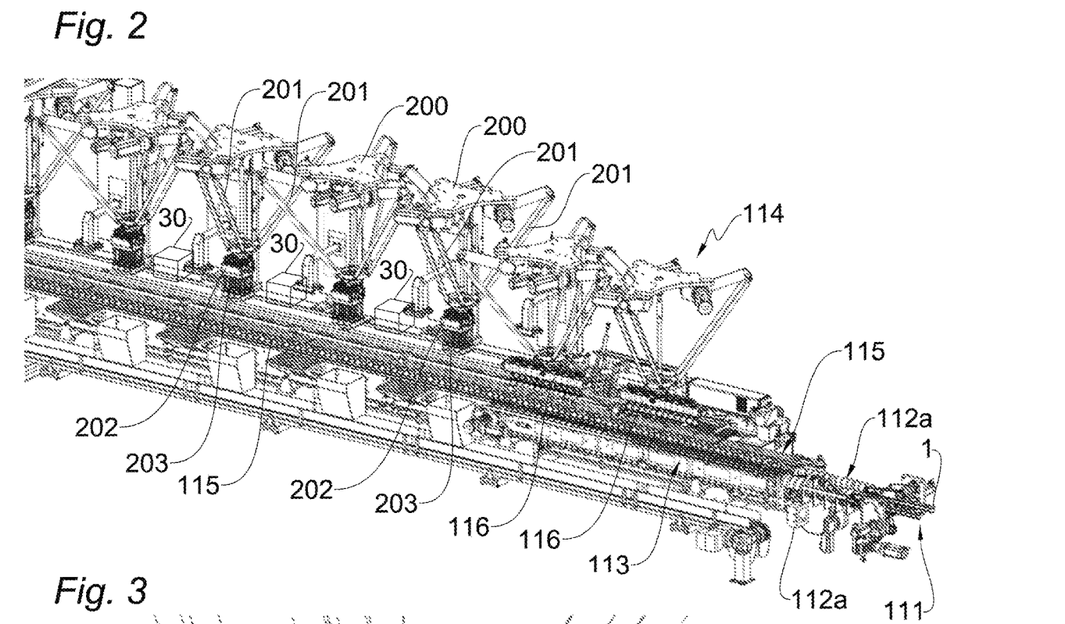
FIG. 2 is a schematic view in lateral perspective and on an enlarged scale of a portion of the packing machine in FIG. 1.

Each transfer device 200 comprises a delta-type robot, which is fixed from above on a support frame (not shown in the accompanying figures), which comprises a plurality of articulated arms 201 and a gripping head 202 which is fixed to an end of the articulated arms 201, according to a configuration that is typical for the delta-type robots.

The gripping head 202 is moved by the articulated arms 201 in trajectories defined by three linear movement axes, while however maintaining its orientation in space fixed (i.e. without rotational movements).

The gripping head 202 comprises a plurality of retention elements 203, each provided to retain a respective article 1, and a movement mechanism overall identified with 204, which is provided to move the retention elements 203 on the gripping head 202 in the directions described in detail below.

In particular, the gripping head 202 is able to remove the articles 1 from the first conveyor belt 115, when the retention elements 203 are spaced apart from one another and coplanar to the support plane of the first conveyor belt 115, and to deposit them in the box 30, in which a support plane of the discharge zone is defined, in a grouped, more compact arrangement, which is obtained by moving the retention elements 203.

In particular, the support plane of the discharge zone may be defined by the bottom of the box 30 or by a layer of articles 1 that are already present in the box 30.

In fact, it should be noted that in a box 30, in addition to a single layer, two so or more superimposed layers can be provided, so as to increase the capacity of each package.

The support plane also defines a deposit direction Z which is substantially perpendicular thereto, generically indicative of the direction in which the articles 1 are deposited in the box 30.

Each retention element 203 is formed like a suction cup and is fixed to a free end 206a of a respective support rod 206, which is connected, at a longitudinally opposed end 206b thereof, to the movement mechanism 204.

In particular, the retention elements 203 are divided into first retention elements 203a, which are configured to retain the articles 1 at the respective head 4 (thus retaining them from above in an upright position), and into second retention elements 203b, which are configured to retain the articles 1 at the respective bottom 2 (thus retaining them from above in an upturned position).

In particular, the first retention elements 203a have a suction cup formation having a first surface, while the second retention elements 203b have a suction cup formation having a second surface, which is smaller than the first surface.

The first and second retention elements 203a, 203b are arranged on the gripping head 202 in alternating position between them, as clearly visible in the accompanying figures.

Figure 3:
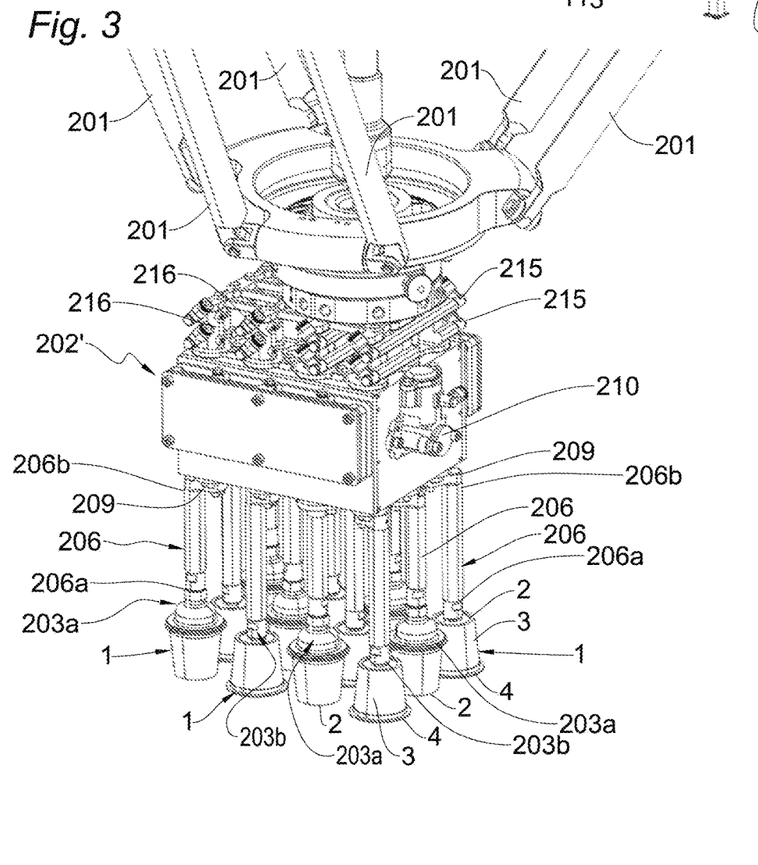
FIG. 3 is a schematic view in lateral perspective and on a further enlarged scale of a gripping head of a transfer device of the packing machine of FIG. 1, with the retention elements in a first operating configuration.
Figure 8:
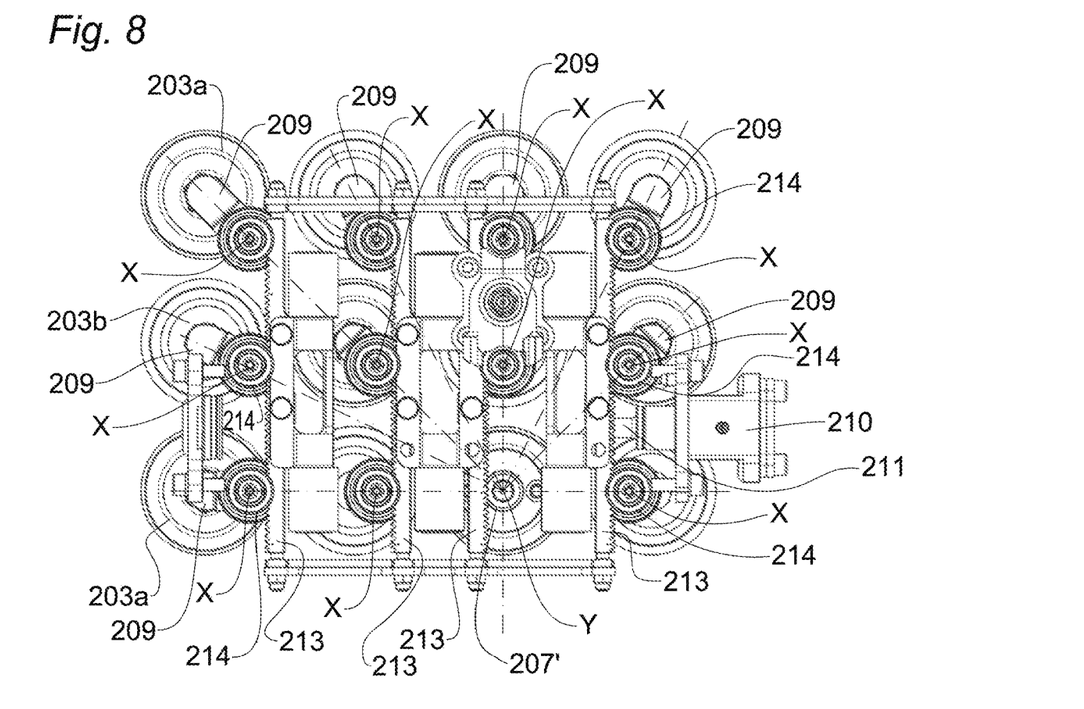
FIGS. 8 and 9 are further simplified and top plan views of the gripping head of FIG. 3, in two respective operating configurations.
Figure 9:
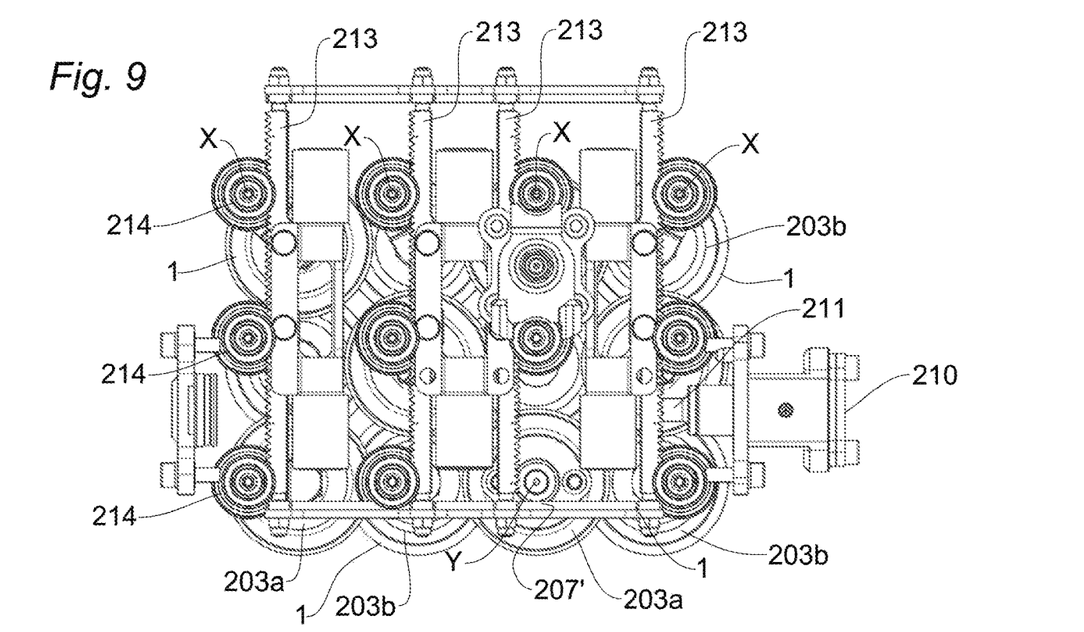

FIGS. 1 to 3 and 8 to 9 illustrate a first example of a gripping head, indicated in FIGS. 3, 8 and 9 as 202', in which the retention elements 203 are arranged in four rows of three retention elements each, and while FIGS. 4 to 7 illustrate a second example of a gripping head, indicated in said FIGS. as 202", in which the retention elements 203 are arranged in three rows of so two retention elements each.

Apart from the number of the retention elements 203 and of their arrangement, the gripping heads 202' and 202" are substantially similar to each other, in particular in the type of movement envisaged for the retention elements 203, and are as whole referred to below with the number 202.

The movement mechanism 204 is provided to move at least some of the retention elements 203 according to two distinct and independent movements: a first movement consists of a movement which is substantially parallel to the support plane defined in the discharge zone, while a second movement consists of a movement in a staggering direction S, which is inclined with respect to said support plane.

In particular, in the preferred example described herein, the movement in the staggering direction S is linear and substantially perpendicular to the support plane, thus coinciding with the deposit direction Z defined above.

In the preferred example described herein, moreover, the support plane defined in the discharge zone is substantially horizontal, so that the reference plane within which the retention elements 203 are moved is substantially horizontal, while the deposit direction Z and the staggering direction S in which the retention elements 203 are moved, are substantially coincident with the vertical direction.

In relation to the first movement mentioned above, the movement mechanism 204 is provided to move the retention elements 203 on the gripping head 202 between a first configuration, in which the retention elements 203 are spaced apart from one another (better visible in FIGS. 3 and 8), and a second configuration, in which the retention elements 203 are so brought close to one another (see FIG. 9).

In particular, the movement mechanism 204 is preferably provided to simultaneously move each retention element 203 between the first and second configuration by means of a rotation movement about a respective rotation axis X.

In particular, the rotation axis X of each retention element 203 is defined by the longitudinal axis of a respective shaft 207, which is rotatably supported on a frame 208 of the gripping head 202 and which extends parallel to the support rod 206.

The shafts 207 are arranged on the gripping head 202 in alignment in successive rows which are equidistant from each other, wherein the shafts 207 comprising each row are also equidistant from each other.

Of course, the number of rows and the number of shafts provided for each row can vary according to specific packing needs. In particular, it is preferred that the arrangement in aligned rows of shafts 207 (and consequently of the retention elements 203) formed on the gripping head 202 corresponds to the arrangement of articles 1 intended to form a single layer within the specific box 30.

The shafts 207, and consequently the rotation axes X defined by them, are all parallel to each other and, in particular, are substantially parallel to the deposit direction Z and, consequently, perpendicular to the support plane on which the articles 1 are to be deposited. Similarly, the shafts 207 are also substantially perpendicular to a support plane which is defined on the first conveyor belt 115 at the removal zone of the articles 1.

The rotation movement of each retention element 203 about its respective rotation axis X is achieved by the provision of a misalignment between the so shaft 207 and the support rod 206.

The connection between shaft 207 and support rod 206 may be made by means of an arm 209 which extends perpendicularly to the rotation axis X between shaft 207 and the end 206b of the support rod 206, as better visible in the gripping head 202', or may be made by fixing the support rod 206 to the shaft 207 in an eccentric position, as better visible in the gripping head 202'.

In the preferred embodiment described herein, it is envisaged that the retention elements 203, during the rotation from the first configuration to the second configuration, are all moved towards a central grouping axis Y, which is parallel to the rotation axes X.

The spacing between the axis of the shaft 207 and the axis of the support rod 206, which in the gripping head 202' is represented by the extent of the arm 209, is a function of the spacing of the respective rotation axis X from the central grouping axis Y. In particular, the greater the spacing of the respective rotation axis X from the central grouping axis Y, the greater the spacing between the axis of the shaft 207 and the axis of the support rod 206.

The central grouping axis Y may preferably coincide with the longitudinal axis of one of the shafts 207, indicated in FIG. 9 by 207', so this shaft is coaxially connected to the respective support rod 206, without the need for its arm 209.

The movement mechanism 204 comprises a motor member 210, for example controlled pneumatically, which is provided to rotate a transmission shaft 211 which is supported with the ability to rotate on the frame 208 of the gripping head 202.

The transmission shaft 211 is provided with toothed crowns engaged by so meshing with respective racks 213, which extend parallel to each row of shafts 207 and in turn engaged by meshing with respective pinions 214 which are coaxially fixed on the shafts 207 to be rotated.

Preferably, racks 213 and pinions 214 are dimensioned such that the movement from the first to the second configuration results in the rotation of the pinions 214 through approximately 180°. In addition, each arm 209 is extended in a direction passing through the central grouping axis Y in both the first and second configuration (situation shown in FIG. 8 with dotted lines).

The movement mechanism 204 is further provided to simultaneously move all of the first retention elements 203*a* with respect to the second retention elements 203*b* in the staggering direction S.

Figures 4, 5:
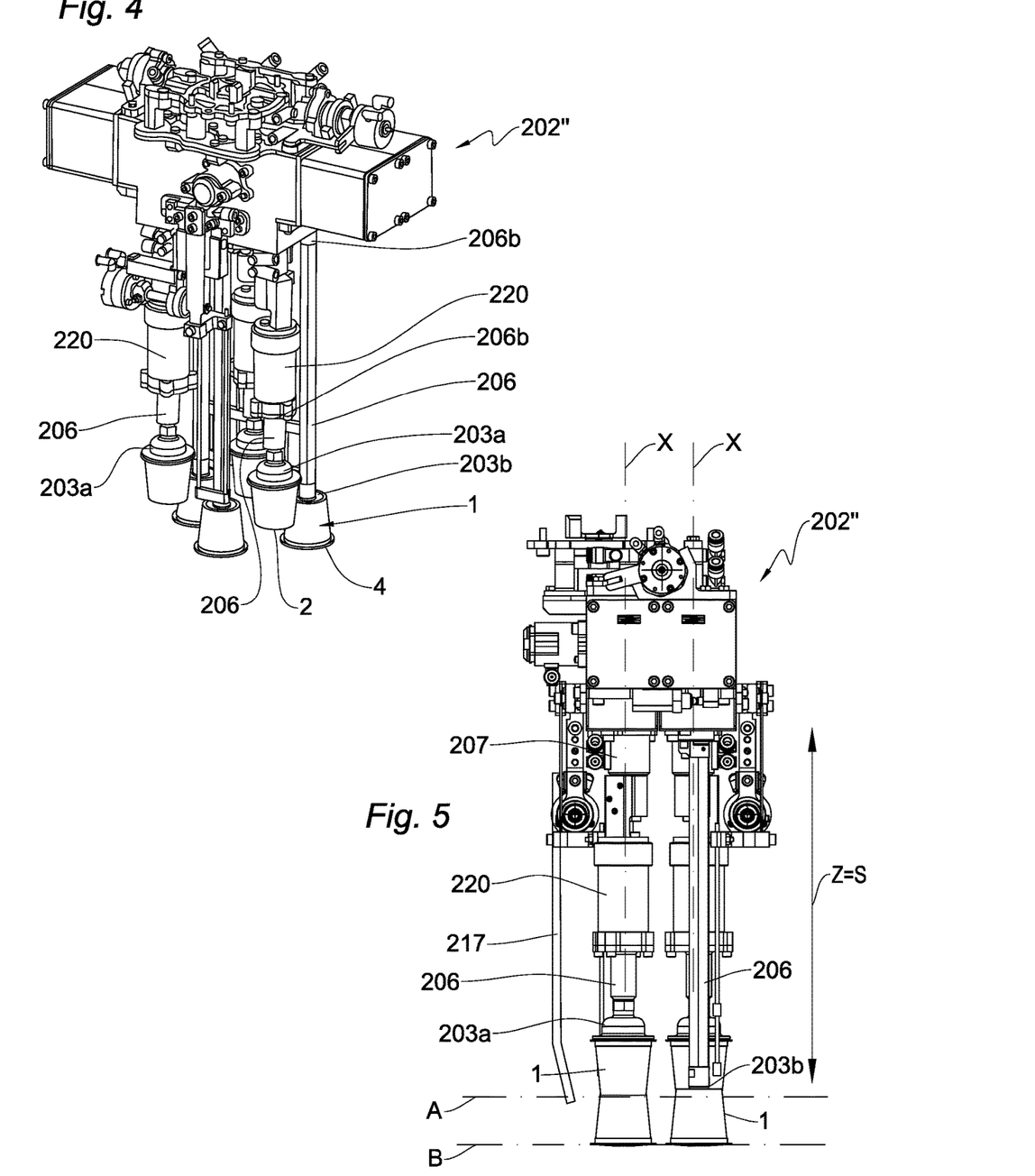
FIG. 4 is a schematic view in lateral perspective of a gripping head similar to the gripping head of FIG. 3, with the retention elements in a second operating configuration.
FIG. 5 is a schematic side elevation view of the gripping head of FIG. 4.
Figure 6:
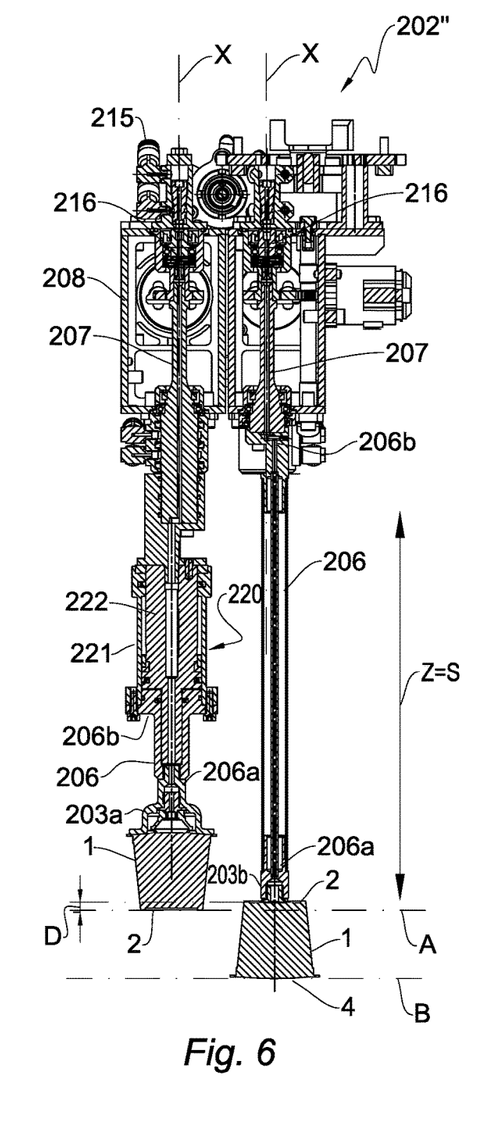
FIG. 6 is a schematic sectional view of the gripping head of FIG. 5.
Figure 7:
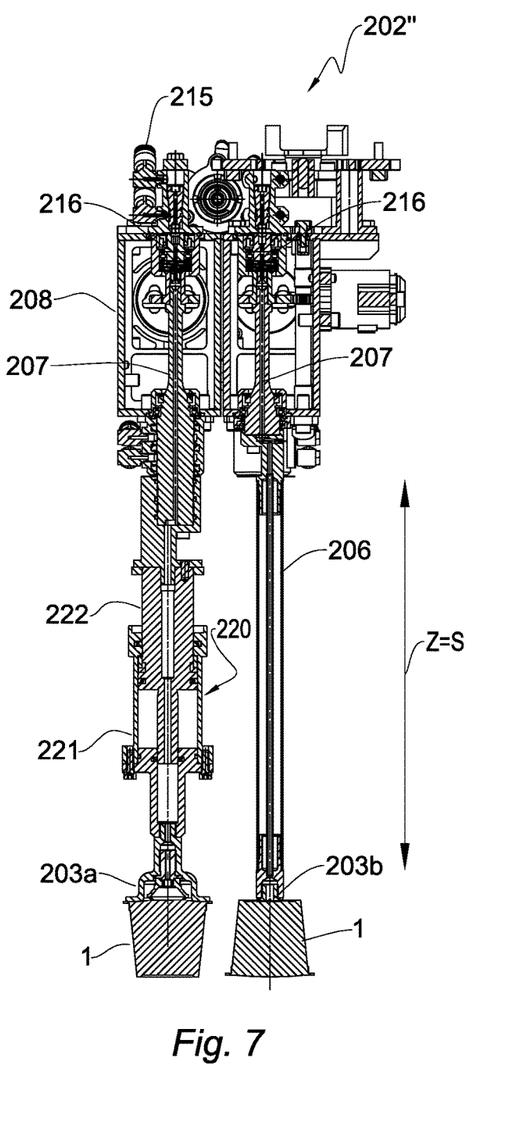
FIG. 7 is a schematic cross-sectional view of the gripping head of FIG. 5 in the first operating configuration.

In particular, as is better visible in FIGS. 4 to 7 referring to the gripping head 202", the first retention elements 203*a* are simultaneously moved between a first position, in which they result substantially coplanar with the second retention elements 203*b* (FIG. 7), and a second position, in which the first retention elements 203*a* and the second retention elements 203*b* are located on respective reference planes A and B which are parallel and spaced apart from one another (FIGS. 5 and 6).

In order to carry out the aforementioned movement, the movement mechanism 204 comprises, for each support rod 206 of the first retention elements 203*a*, a respective actuating member 220 which is provided to move the support rod 206 in the staggering direction S.

In particular, in the example embodiment illustrated herein, the actuating member 220 is formed by a double-acting pneumatic actuator comprising a cylinder 221 and a piston 222 which is engaged slidingly within the cylinder 221.

One between the cylinder 221 and the piston 222 is integral with shaft 207 and the other one between the cylinder 221 and the piston 222 is integral with the support rod 206.

It is also envisaged that the actuating member 220 may be formed by control mechanisms of different type, for example of the mechanical type, such as a rack and pinion gear, or of the electromagnetic or hydraulic type.

The extent of movement in the staggering direction S of the first retention elements 203*a* with respect to the second retention elements 203*b*, which remain fixed with respect to the gripping head 202, is chosen according to the specific formation of the articles 1 to be transferred by the transfer device 200. In particular, it is chosen so as to allow the greatest possible degree of compaction of the articles 1 when the retention elements 203 are subsequently moved into the second configuration, in an approached position. In the case described herein, wherein the articles 1 have a truncated conical shape, with a smaller base formed by the bottom 2 and a larger base formed by the head 4, and are removed by the first conveyor belt 115 with the "chequered" removal pattern described above, it is envisaged that the first retention elements 203*a* are moved in the staggering direction S until the orthogonal projection of the articles 1 retained by the first retention elements 203*a* in a plane parallel to the storage direction Z is partially superimposed on the orthogonal projection of the articles that are retained by said second retention elements only near the respective bottoms 2.

In particular, the superposition between the aforementioned orthogonal projections, indicated by D in FIG. 6, may be only a few millimetres, for example approximately 5 mm.

In this way, the second position of the movement of the first retention elements 203*a* in the staggering direction S is defined.

The transfer device 200 further comprises a spreader element 217 which extends from the gripping head 202 in accordance with the support rods 206 of the retention elements 203 and in a position external thereto (see FIG. 5).

The spreader element 217 is provided to abut the box 30 at the closing panel thereof, which, appropriately, is located on the side of the box 30 opposite the first conveyor belt 115.

In this case, the spreader element 217 comprises a rod which is fixed externally to the gripping head 202, on the side facing the second conveyor belt 107 and which extend as far as a height that is higher than the level of the support plane of the articles 1, so as not to interfere with the same. Furthermore, preferably, the spreader element 217 is placed centrally between two support rods 206 so as to avoid interference with the articles 1 during the removal step or movement step the retention elements 203.

In order to retain the articles 1 during the transfer from the removal zone to the discharge zone, each retention element 203 is selectively connected to a pressure reduction circuit 215, associated with the gripping head 202, by means of a respective shut-off valve 216.

In particular, the shut-off valve 216 is capable of putting the pressure reduction circuit 215 in communication with the respective retention element 203 by means of a conduit which is formed inside the respective support rod 206, the shaft 207, and, if present, the arm 209 and the actuating member 220.

The articles 1 are then retained on the respective retention elements 203 thanks to the suction action carried out by the pressure reduction circuit 215 once the retention elements 203 are placed on the bottom 2 or on the head 4 of the articles 1 to be transferred.

Each shut-off valve 216 is independently operable independently of the other shut-off valves, so that each retention element 203 can be selectively activated and deactivated in order to retain or not retain an article 1 in engagement independently of the other retention elements 203.

Each transfer device 200 of the packing machine 1 operates as described below.

The gripping head 202 is moved by the arms 201 at the removal zone, above the first conveyor belt 115 on which the articles 1 to be removed are arranged in a chequered pattern.

In this position, the retention elements 203 are moved into the first position, so that they are all substantially coplanar to the support plane of the first conveyor belt 115, and in the first configuration, so that the spacing between them corresponds to the spacing between the articles arranged on the first conveyor belt 115.

The gripping head 202 is then lowered onto the articles 1, equalizing the speed of the first conveyor belt 115, which maintains its movement unchanged, until it abuts with the retention elements 203 of the articles 1 to be removed. The first and the second retention elements 203*a* and 203*b* are alternated with each other, mirroring the chequered arrangement of the articles 1, so that each first retention element 203*a* is lowered onto an article 1 in upright position and each second retention element 203*b* is lowered onto an article 1 in upturned position.

All the shut-off valves 216 of the retention elements 203 to be activated are thus opened, so as to put the retention elements 203 in communication with the pressure reduction circuit 215 and to suck in the articles 1 to be removed. If necessary, the gripping head 202 may be moved over another group of articles 1 brought within the removal zone by the first conveyor belt 115, so as to remove further articles 1 with the retention elements 203 that are still free and to complete the composition of a layer of articles 1 to be deposited in the box 30. Of course, the operation of completing the layer of articles 1 on the gripping head 202 may require one or more removal steps, as a function of the composition of the layer (and thus, more generally, as a function of the size of the box 30 to be filled).

By way of example, a transfer device 200 provided with the gripping head 202' will be able to form a complete layer of articles 1 with two successive removal steps, whereas a transfer device 20 provided with the gripping head 202" will be able to form a complete layer of articles 1 with only one removal step.

Once the removal of the articles 1 to be deposited is ended, the gripping head 202 is moved towards the discharge zone, at a box 30 brought onto the second conveyor belt 107.

During the movement of the gripping head 202 towards the discharge zone, the first retention elements 203a are simultaneously moved in the staggering direction S from the first position (FIG. 7) to the second position (FIGS. 4 to 6), after which all the retention elements 203 are simultaneously rotated in 1o the second configuration, so as to bring the articles 1 close to one another and to compact them in a grouped arrangement (clearly visible in FIG. 9), which is suitable for allowing their rapid insertion into the box 30. The two movements of the retention elements 203 may be carried out in sequence or in more or less superimposed time intervals.

The movement from the first to the second position is obtained thanks to the action of the actuating members 220, which, by moving the piston 222 inside the cylinder 221, lift the respective first retention elements 203a towards the corresponding shafts 207.

The rotation of the retention elements 203 about their respective rotation axes X is obtained by controlling the rotation of the motor member 210 which, by means of the transmission shaft 211, linearly moves the racks 213 and, thanks to the engagement with the pinions 214, causes the rotation of the shafts 207 and thus of the retention elements 203.

Upon reaching the discharge zone with the retention elements 203 which have been moved to the second configuration, the gripping head 202 is moved towards the box 30, equalizing the speed of the second conveyor belt 107.

Each box 30 is positioned onto the second conveyor belt 107 with its respective closing panel open, in a vertical position, which is positioned parallel and on the opposite side to the first conveyor belt. At this point, the spreader element 217 abuts the closing panel of the box 30, so as to bend it slightly with respect to the vertical plane and thus obtain the curvature also of the creasing line which connects the closing panel to the wall below. The curvature of the creasing line prevents the closing panel from folding outwards so that the deformation of the closing panel is also so transmitted to the wall to which it is connected. This leads to a temporary bulging of this wall and consequently to a temporary widening of the opening of box 30.

The gripping head 202 is then lowered onto the box 30 and deposits the articles 1 in group on the support plane defined therein.

Since the first retention elements 203a are raised with respect to the second retention elements 203b, the support plane is reached first by the articles 1 transported by the second retention elements 203b.

The articles 1 are released by deactivating the retention elements 203 by closing the shut-off valves 216.

At this point, the first retention elements 203a are moved in the deposit direction Z in the first position, so as to favour the movement of the articles 1 transported by them towards the support plane, in a condition of coplanarity with the articles 1 that have already been deposited by the second retention elements 203b.

The gripping head 202 is then lifted and as it is moved towards the first conveyor belt 115 for a new removal of articles, the retention elements 203 are spaced apart from one another by rotating them in the first configuration.

In the meantime, the closing panel of the container is disengaged from the spreader element 217 and can therefore return to its starting configuration, which is substantially flat, and is thus able to rotate about the creasing line which connects it to the wall below, for example to close the box 30 again before being sent to the final packing.

In a different operating mode, the transfer device 200 according to the present invention may be used to remove the articles 1 from a box 30, in particular an incomplete or damaged box, and to deposit the articles 1 at, for so example, an auxiliary shelf, from which, for example, the articles 1 may subsequently be removed to be inserted inside a subsequent box 30. In this case, the removal zone is defined in box 30 and the discharge zone is defined in the auxiliary shelf. It is understood that instead of an auxiliary shelf, the articles may be deposited in another receptacle or on a conveyor belt. It goes without saying that a person skilled in the art may, in order to meet specific and contingent application requirements, make further modifications and variants of the above-described invention within the scope of protection as defined by the following claims.

The invention claimed is:

1. A transfer device to transfer a plurality of articles by removing the plurality of articles from a removal zone and depositing the plurality of articles in a discharge zone, wherein a support plane and a deposit direction substantially perpendicular to said support plane are defined at the discharge zone, said transfer device comprising:
   a gripping head movable between said removal zone and said discharge zone, the gripping head comprising retention elements, the retention elements comprising a plurality of first retention elements and a plurality of second retention elements and each retention element configured to simultaneously retain a single respective article of said plurality of articles, the gripping head configured to retain said plurality of articles, and
   a movement mechanism configured to simultaneously move said plurality of first retention elements with respect to said plurality of second retention elements in a staggering direction having a non-null component parallel with said deposit direction while retaining said plurality of articles,
wherein:
   said plurality of first retention elements are configured to move in said staggering direction between a first position, wherein said plurality of first retention elements are coplanar with said plurality of second retention elements, and a second position, wherein said plurality of first retention elements and said plurality of second retention elements are located in respective reference planes parallel with and spaced apart from each other, and said plurality of second retention elements are not movable in said staggering direction with respect to said gripping head.

2. The transfer device according to claim 1, wherein said movement mechanism comprises an actuating member for moving said plurality of first retention elements in said staggering direction.

3. The transfer device according to claim 1, wherein said staggering direction is substantially parallel with said deposit direction.

4. The transfer device according to claim 1, wherein said movement mechanism is further configured to move at least one of said retention elements in directions located in a reference plane substantially perpendicular to said deposit direction.

5. The transfer device according to claim 4, wherein said retention elements are moved inside said reference plane between a first configuration, wherein said retention elements are spaced apart from one another, and a second configuration, wherein said retention elements are brought close to one another.

6. The transfer device according to claim 5, wherein said movement mechanism is configured to move said retention elements between said first configuration and said second configuration by rotation about respective rotation axes.

7. The transfer device according to claim 1, wherein said discharge zone, in which said plurality of articles are deposited, is defined in a container.

8. The transfer device according to claim 7, wherein at least one spreader element extends from said gripping head in accordance with said retention elements and is configured to abut said container and to widen the opening thereof.

9. The transfer device according to claim 1, wherein the plurality of articles have a tapered formation from a larger base up to a smaller base, and wherein, in said second position, an orthogonal projection of the articles retained by said plurality of first retention elements in a plane parallel with said deposit direction is partially superimposed on the orthogonal projection of the articles retained by said plurality of second retention elements only near said smaller base.

10. The transfer device according to claim 1, wherein each of said retention elements are configured to be selectively activated and deactivated in order to retain or not to retain in engagement one of said plurality of articles independently of the other retention elements.

11. A packing machine for articles, comprising at least one transfer device according to claim 1.

12. A method for transferring articles from a removal zone to a discharge zone, wherein a support plane and a deposit direction substantially perpendicular to said support plane are defined at the discharge zone, said method comprising:

providing a transfer device comprising a gripping head comprising first retention elements and second retention elements, removing said articles from said removal zone by the retention elements, moving said first retention elements simultaneously with respect to said second retention elements in a staggering direction having a non-null component parallel with said deposit direction from a first position, in which the first retention elements and the second retention elements are coplanar, and a second position, in which the first retention elements and the second retention elements are located in respective parallel and spaced apart planes, moving said retention elements inside a reference plane substantially perpendicular to said deposit direction between a first configuration, wherein said retention elements are spaced apart from one another, and a second configuration, wherein said retention elements are brought close to one another, moving the articles towards the support plane when the first retention elements are in the second position, and depositing said articles on said support plane when said first retention elements are in said first position.

13. The method according to claim 12, wherein said articles are removed by said first retention elements and second retention elements while said removal zone is moving.

14. The method according to claim 12, wherein said articles are deposited by said first retention elements and said second retention elements on said support plane while said support plane is moving.

15. A method for packing articles in a container, comprising:

transferring the articles in accordance with the method according to claim 12.

* * * * *